(12) United States Patent
Weitzig et al.

(10) Patent No.: US 8,798,772 B2
(45) Date of Patent: Aug. 5, 2014

(54) ELECTRODE CONNECTION, IN PARTICULAR FOR AN ELECTRODE CATHETER

(75) Inventors: Pierre Weitzig, Berlin (DE); Jochen Palm, Mahlow (DE); Detmar Jadwizak, Erkner (DE); Carsten Fruendt, Berlin (DE)

(73) Assignee: Biotronik SE & Co. KG, Berlin (DE)

( * ) Notice: Subject to any disclaimer, the term of this patent is extended or adjusted under 35 U.S.C. 154(b) by 107 days.

(21) Appl. No.: 13/180,725

(22) Filed: Jul. 12, 2011

(65) Prior Publication Data
US 2012/0028512 A1 Feb. 2, 2012

Related U.S. Application Data

(60) Provisional application No. 61/367,889, filed on Jul. 27, 2010.

(51) Int. Cl.
*A61N 1/00* (2006.01)
*H01R 13/58* (2006.01)
*H01R 9/05* (2006.01)
*A61N 1/05* (2006.01)
*H01R 4/50* (2006.01)

(52) U.S. Cl.
CPC ............ *A61N 1/056* (2013.01); *H01R 2201/12* (2013.01); *H01R 4/5016* (2013.01)
USPC ........................... 607/127; 439/583; 439/460

(58) Field of Classification Search
USPC .......... 439/816, 459, 460, 583–585; 607/122, 607/127
See application file for complete search history.

(56) References Cited

U.S. PATENT DOCUMENTS

| 4,566,467 | A | 1/1986 | DeHaan |
| 5,569,883 | A | 10/1996 | Walter et al. |
| 6,505,081 | B1 | 1/2003 | Das |
| 7,580,758 | B2 * | 8/2009 | Junge et al. ................... 607/127 |
| 2005/0228469 | A1 | 10/2005 | Zarembo et al. |

FOREIGN PATENT DOCUMENTS

DE 20 2005 020 835 10/2006

OTHER PUBLICATIONS

European Search Report and Notes to the European Search Report on European Patent Application No. EP 11 17 2361, dated Oct. 10, 2011 (7 pages).

* cited by examiner

*Primary Examiner* — Felix O Figueroa
(74) *Attorney, Agent, or Firm* — Buchanan Ingersoll & Rooney PC

(57) ABSTRACT

An electrode connection for an electrode catheter including an electrode, a line for electrical signals configured as a coil having an electrode end connected to the electrode, and a fixation device for the electrode end of the coil on the electrode, wherein the fixation device includes an inner sleeve, on which the electrode end of the coil sits, and a squeeze ring, which acts upon the electrode end of the coil, establishing an electrical contact with the electrode and mechanical clamping on the inner sleeve.

12 Claims, 5 Drawing Sheets

ELECTRODE CONNECTION, IN PARTICULAR FOR AN ELECTRODE CATHETER

CROSS-REFERENCE TO RELATED APPLICATIONS

This patent application claims the benefit U.S. Provisional Patent Application No. 61/367,889, filed on Jul. 27, 2010, which is hereby incorporated by reference in its entirety.

TECHNICAL FIELD

The invention relates to a form-fitting electrode connection, in particular for an electrode catheter, comprising an electrode, a line for electrical signals, embodied as a coil connected to the electrode, and a fixation device for the electrode end of the coil to the electrode.

BACKGROUND

With regard to the background of the invention, it should be pointed out that the mechanical and electrical connection of the line embodied as a coil in an electrode catheter having a head or ring electrode—for example, in a cardiac pacemaker electrode—must be particularly reliable because an interruption in this connection would lead to failure of the electrode catheter, which could have fatal consequences for the patient. Furthermore, such a defect would necessitate replacement of the electrode catheter, which would in turn necessitate an interventional procedure with all the usual accompanying circumstances, risks and consequences for the patient.

Mechanical and electrical connections of the coil to the electrode based on welding and crimping processes are fundamentally known and customary through obvious prior use. Although such connections are quite acceptable with regard to their reliability, these known approaches still have various disadvantages.

In welding, the material of the coil must naturally be fundamentally weldable. To this extent, welding processes cannot be used with coil wires made of various core and sheath materials, which have different melting points. Furthermore, the materials to be joined must be coordinated with one another, so that they can be welded to one another. This depends on the melting points of the welding partners and the diffusion of alloy elements therein. This may lead to embrittlement of the joining partners in the area of the heat influence zone. Components having very thin walls within the electrode device are fundamentally very problematical to weld. Another disadvantage is the inability to inspect such a welded joint. It is quite possible for an initial inspection for mechanical strength and electrical contact to be positive even if the weld is defective in the long run. Finally, even the smallest impurities on the components may lead to incomplete welded joints and thus result in manufacturing rejects.

The crimping mentioned above has safety deficiencies from the standpoint of production technology inasmuch as the quality of the joint usually depends on the hardness of the components. Furthermore, small diameters of components involved in a crimped connection are not possible because it is necessary to provide certain minimum wall thicknesses and a design of the joint adapted to the crimping technique together with an essential supporting structure and a separate crimping sleeve.

Against the background of the problems associated with the state of the art described above, an object of the present invention is to improve upon an electrode connection in its fixation device for the electrode end of the coil to the electrode, so that a secure mechanical and electrical connection of the coil to the electrode can be created, regardless of the materials used.

SUMMARY

The object is achieved by an electrode connection having a fixation device, comprising:
an inner sleeve, on which the electrode end of the coil sits, and
a squeeze ring, which acts on the electrode end of the coil, establishing electrical contact with the electrode and mechanical clamping on the inner sleeve.

The inventive electrode connection avoids the problems of the state of the art described herein. First, no welded joint is used, so the fixation device is able to establish a connection between the wire coil and the electrode regardless of the materials used. Second, since this is a purely mechanical process, better monitoring ability is also provided, which essentially leads to an improvement in the quality of the joint.

Certain dependent claims (e.g., claims 2-6) characterize a first advantageous implementation of the basic principle of the electrode connection as defined in independent claim 1. This first variant is based on a type of form-fitting connection between the coil end, which is widened due to the outer cone of the inner sleeve, with the squeeze ring, which is provided with a suitable inner cone and is pushed onto the widened coil end. In particular, the squeeze ring is pushed onto the coil end with deformation of the line forming the coil end, so that an intimate and fixed connection is established in the manner of a form-fitting connection between the inner sleeve, the wire coil and the squeeze ring.

A second variant of the basic concept as characterized in other dependent claims (e.g., claims 7-12) is based on a type of screw connection, in that the electrode end of the coil, which is wound openly, is screwed onto the inner sleeve by engaging a threaded element behind it, and the section of the coil element screwed over the threaded element is acted upon by the squeeze ring, in particular, axially against the threaded element. Due to the resulting compression of the openly wound coil end, in particular, up to blocking by the squeeze ring, a type of self-locking effect is induced in the screw connection between the wire coil and the inner sleeve, making any release of the mechanical and thus electrical connection between the inner sleeve and the coil end fundamentally impossible.

Various other objects, aspects and advantages of the present invention can be obtained from a study of the specification, the drawings, and the appended claims.

DESCRIPTION OF THE DRAWINGS

Additional features, details and advantages of the invention are derived from the following description of exemplary embodiments on the basis of the accompanying drawings, in which.

DETAILED DESCRIPTION

Figure 1:
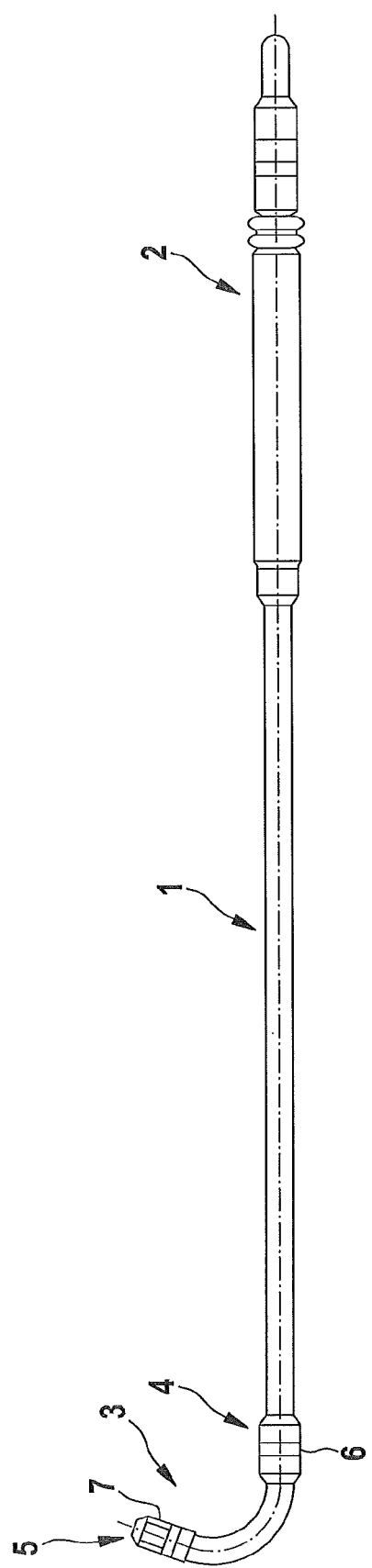
FIG. 1 shows a side view of an electrode catheter.

As shown in FIG. 1, in particular, the electrode catheter, which is used for cardiac therapy, comprises an elongated tubular catheter body 1, which is provided with a connecting plug 2 at its proximal end for connection to a corresponding implant. A ring electrode 4 is arranged in the area of the distal end 3, and there is a head electrode 5 directly at the tip of the distal end 3. These electrodes 4 and 5 serve to deliver or measure an electrical signal, i.e., an electro-cardiac signal in the present case, via their respective external electrode contact surfaces 6 and 7, for example, for reliable and effective defibrillation or diagnostic testing for early detection of atrial fibrillations and progression of cardiac insufficiency.

Figure 2:
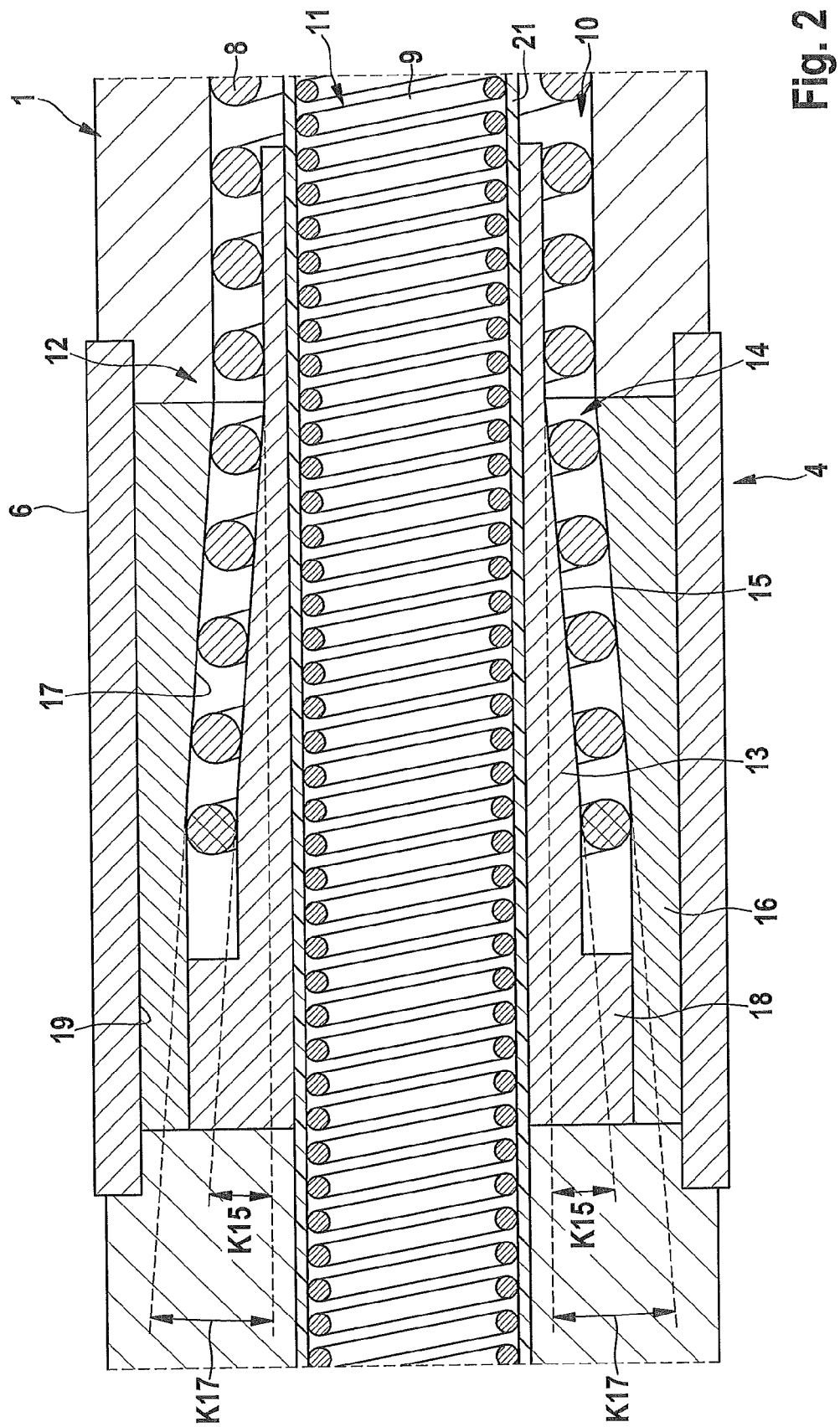
FIGS. 2 and 3 show enlarged details of longitudinal axial sections of the electrode catheter in the area of a ring and head electrode in a first embodiment.
Figure 3:
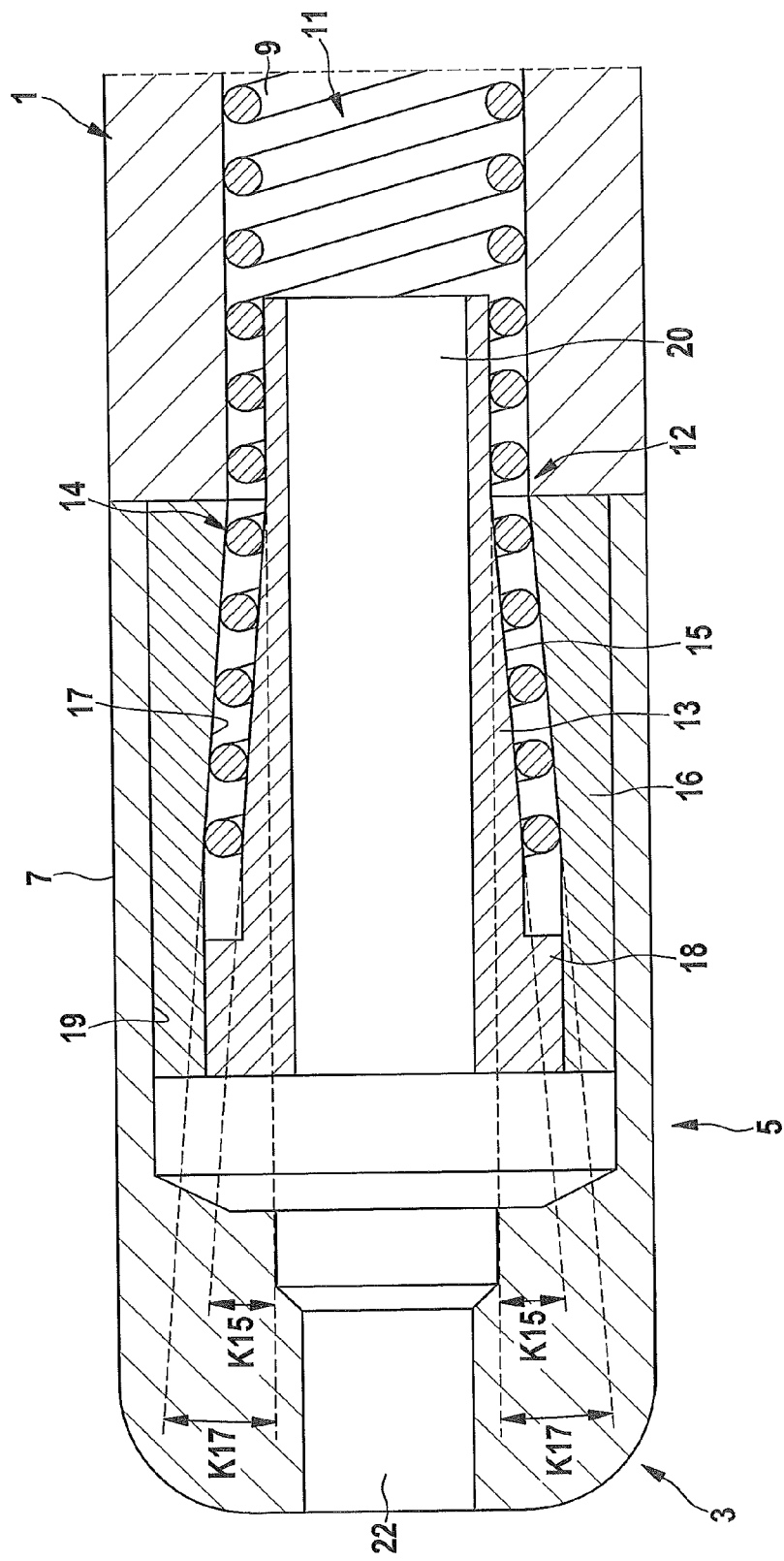

On the basis of FIGS. 2 and 3, a first embodiment of the connection of electrodes 4 and 5 to corresponding feeder lines 8 and 9 is explained. Two such feeder lines 8 and 9 in the form of coils 10 and 11 sitting coaxially one inside the other are thus guided from proximally in the tubular catheter body 1. The outer coil 10, with the feeder line 8, serves to form a connection to the ring electrode 4, as illustrated in FIG. 2. The inner coil 11 is continued in the distal direction through the electrode 4 with insulation.

The fixation device, which is illustrated in FIG. 2 and is labeled as 12 on the whole, has an inner sleeve 13 on which the electrode end 14 of the coil 10 sits. The inner sleeve 13 is provided with an outer cone 15, which is widened in the distal direction and on which the coil end 14 is placed in assembly and, therefore, also sits with a widened conical shape.

A squeeze ring 16, which is provided with an inner cone 17 that also widens in the distal direction, is pushed onto the module comprising the inner sleeve 13 and the electrode end 14 of the coil 10. The squeeze ring 16 is threaded onto the coil 10 before the electrode end 14 is pushed onto it and, after connecting the coil 10 to the inner sleeve 13, it is pushed further in the distal direction, and the widened coil end is more or less squeezed onto it. The feeder line 8 forming the coil end 14 is deformed slightly, so that a type of form-fitting connection is established between the inner sleeve 13, the coil end 14 and the squeeze ring 16, achieving a mechanically stable and electrically secure connection between these components, which are made of an electrically conductive material. In the distal end area, the squeeze ring 16 is secured by placing it on a bearing shoulder 18 on the end of the inner sleeve 13 facing distally.

The cone angles K15 and/or K17 on the outer cone 15 of the inner sleeve 13 and/or on the inner cone 17 of the squeeze ring 16 are shallow and amount to approximately 15° and, in particular, preferably approximately 10°, for example. Furthermore, they match in their angle values. In one form, it is contemplated that the angles be smaller than 15°.

To establish an electrical connection between the coil 10 and the ring electrode 4, on its side 19 facing radially outward the squeeze ring 16 is connected to the ring electrode 4 in an electrically conducting manner, for example, by a physically bonded connection.

The inner coil 11 of the feeder line 9 is continued in the distal direction through the inner bore 20 of the inner sleeve 13 to the head electrode 5 with an insulating tube 21 in between (see FIG. 3).

FIG. 3 shows a fixation device 12 like the fixation device explained with reference to FIG. 2 for connecting the inner coil 11 to the feeder line 9 on the head electrode 5. This design corresponds to that of the fixation device 12 according to FIG. 2, and to the extent that the description of the fixation device 12 from FIG. 2 can be applied fully to the design shown in FIG. 3, reference can be made thereto in order to avoid repetition. Components having the same design are labeled with identical reference numerals.

The inner bore 20 of the inner sleeve 13 of the fixation device 12 on the head electrode 5 serves to pass through a mandrel and/or guide wires for the electrode catheter. A central head bore 22 in the head electrode 5 is aligned with the inner bore 20.

Figure 4:
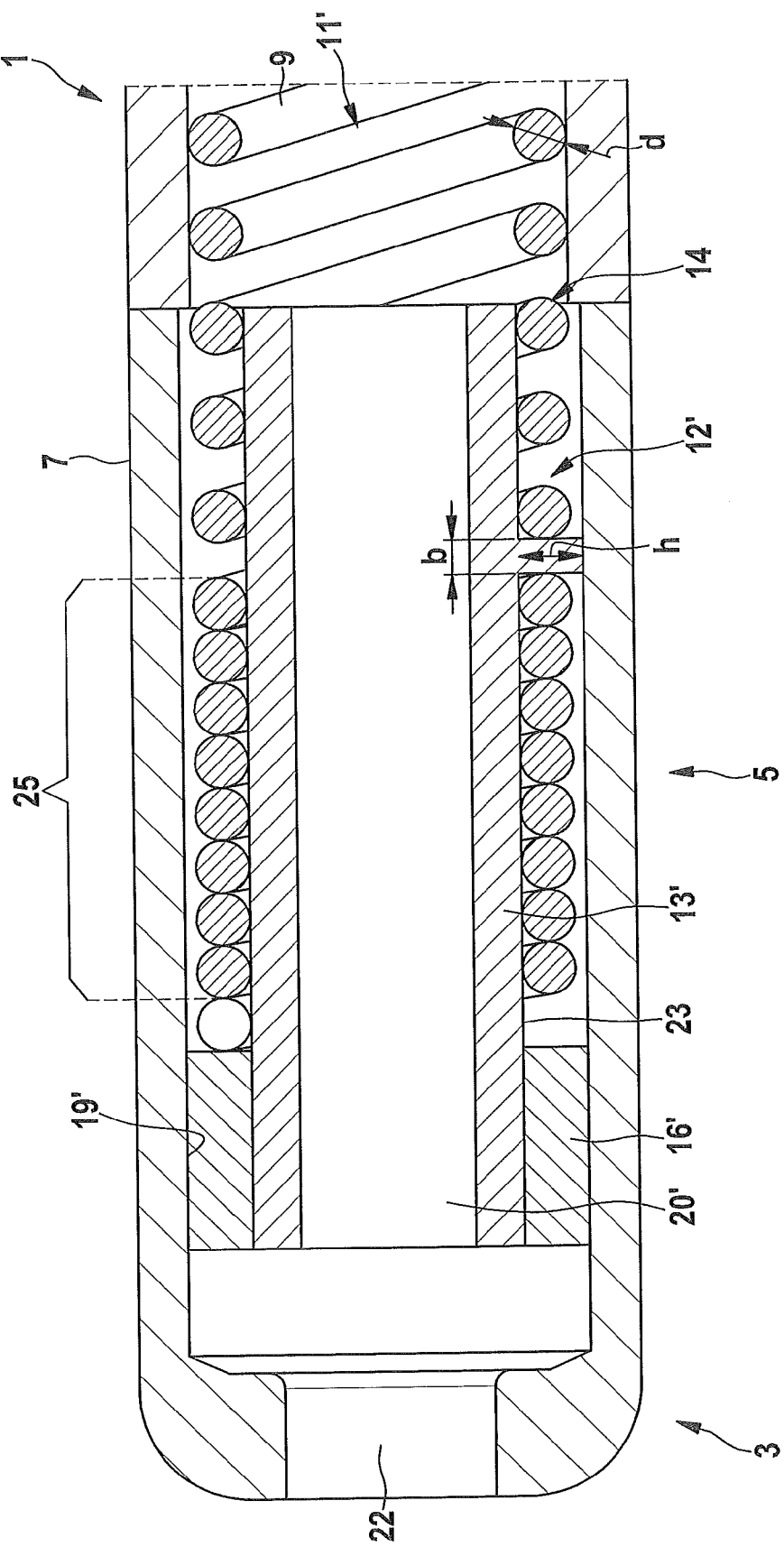
FIG. 4 shows an enlarged detail of a longitudinal, axial section of an electrode catheter in the area of the head electrode in a second embodiment.
Figure 6:
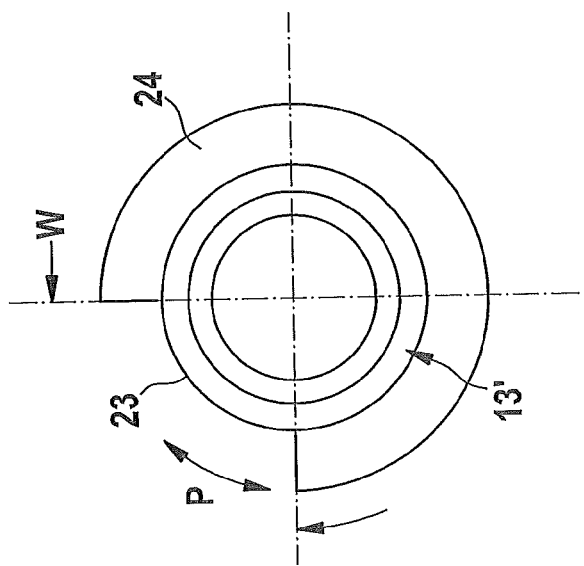
FIG. 6 shows an axial view of the inner sleeve according to FIG. 5.
Figure 5:
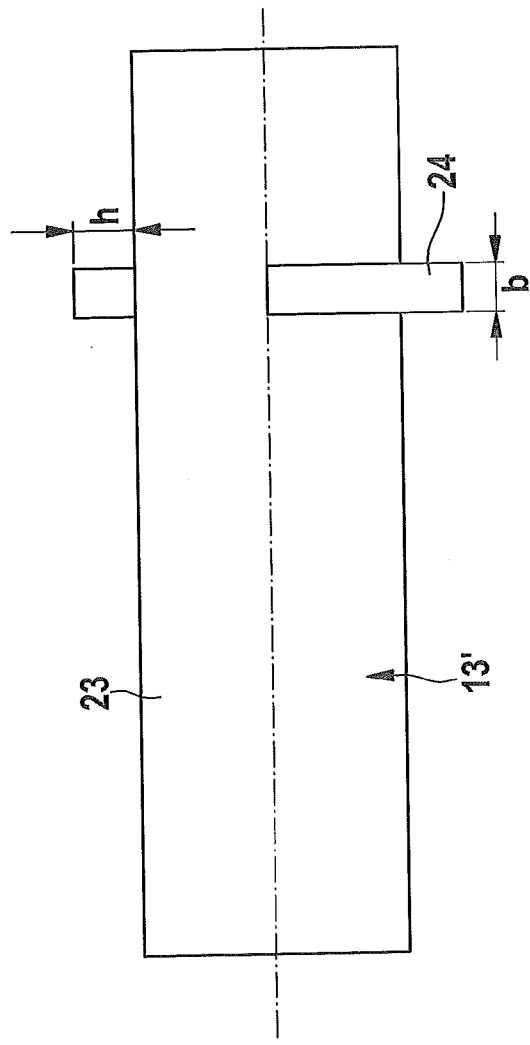
FIG. 5 shows a side view of the inner sleeve used in the fixation device according to FIG. 4.

FIGS. 4-6 show an alternative embodiment of a fixation device 12' for connecting a coil 11 of the feeder line to the head electrode 5. The fixation device 12' has an inner sleeve 13', which is embodied not as a cone but instead as a cylindrical sleeve with regard to its base body. At approximately one-fourth of its total length, a threaded element in the form of a web 24 running over a partial circumference of the inner sleeve 13' is designed on the lateral surface 23 of the inner sleeve 13'. As shown in FIGS. 5 and 6, in particular, the web 24 runs over an angle W of approximately 240° to 300° and, preferably 270°, in the peripheral direction P around the inner sleeve 13'. The web has a height "h", which is slightly greater than the diameter "d" of the feeder line 9 forming the coil. Its width "b" corresponds approximately to the diameter "d".

As shown more clearly in FIG. 4, the coil 11' is provided with winding gaps and may thus be screwed onto the inner sleeve 13' over the threaded element web 24 until multiple windings have passed by the web 24. Then, a squeeze ring 16' is pushed onto the distal end of the inner sleeve 13' against the screwed-on coil windings 25, so that the coil windings 25 are acted upon in such a way that they are compressed on block. This state is illustrated in FIG. 4. Because of this compression, the winding package 25 is secured between the squeeze ring 16' and the web 24 by a self-locking effect, so that the coil 11' cannot be un-screwed and, therefore, it is impossible to loosen the connection between it and the inner sleeve 13'.

The squeeze ring 16' is secured on the inner sleeve 13' by suitable measures, such as, for example, a bonded connection. Likewise, the side 19' of the squeeze ring 16' facing radially outward is again securely connected electrically and mechanically to the head electrode 5 by, for example, a bonded connection.

The inner bore 20' of the inner sleeve 13' together with the head bore 22 of the head electrode 5 in turn serves to provide passage for a mandrel or guide wires for the electrode catheter.

It will be apparent to those skilled in the art that numerous modifications and variations of the described examples and embodiments are possible in light of the above teachings of the disclosure. The disclosed examples and embodiments are presented for purposes of illustration only. Other alternate embodiments may include some or all of the features disclosed herein. Therefore, it is the intent to cover all such modifications and alternate embodiments as may come within the true scope of this invention, which is to be given the full breadth thereof. Additionally, the disclosure of a range of values is a disclosure of every numerical value within that range.

We claim:
1. An electrode connection for an electrode catheter, comprising:
 an electrode;
 a line for electrical signals configured as a coil having an electrode end connected to the electrode; and
 a fixation device for the electrode end of the coil on the electrode, wherein the fixation device comprises:

an inner sleeve, on which the electrode end of the coil sits; and a squeeze ring, which acts upon the electrode end of the coil, establishing an electrical contact with the electrode and a mechanical clamping of the coil on the inner sleeve via a force acting in a radial direction with respect to a length of the coil, wherein the inner sleeve has an outer cone surface, which widens starting from an end engaging with the coil toward a distal end of the electrode catheter forming an outer cone angle and on which the coil end also sits with a conical widening, and wherein the squeeze ring has an inner cone surface which lessens starting from an end engaging with the coil toward a distal end of the electrode catheter forming an inner cone angle, such that the squeeze ring secures the coil end between the inner and outer cone surfaces, the squeeze ring pushed axially onto the widened coil end, and wherein the squeeze ring is connected mechanically and electrically to the electrode on a side of the squeeze ring facing radially outward.

2. The electrical connection according to claim 1, wherein the squeeze ring is pushed onto the coil with deformation of the line forming the coil end.

3. The electrode connection according to claim 1, wherein the squeeze ring is secured in a fixation position on a bearing shoulder on the inner sleeve.

4. The electrode connection according to claim 1, wherein cone angles on the outer cone of the inner sleeve and on the inner cone of the squeeze ring are smaller than 15°.

5. The electrode connection according to claim 4, wherein the cone angles on the outer cone of the inner sleeve and on the inner cone of the squeeze ring are equal.

6. The electrode connection according to claim 1, wherein the electrode end of the openly wound coil is screwed onto the inner sleeve by engaging behind a threaded element on the inner sleeve, and the section of the coil end which is screwed onto the threaded element is acted upon by the squeeze ring.

7. The electrode connection according to claim 6, wherein the section of the coil end which is screwed over the threaded element is acted upon axially with compression against the threaded element.

8. The electrode connection according to claim 6, wherein the section of the coil end screwed over the threaded element is compressed on block.

9. The electrode connection according to claim 6, wherein the threaded element is formed by a web running in a peripheral direction over a partial circumference of the inner sleeve.

10. The electrode connection according to claim 9, wherein the web runs over an angle of approximately 240° to 300° in the peripheral direction.

11. The electrode connection according to claim 9, wherein the web runs over an angle of approximately 270° in the peripheral direction.

12. The electrode connection according to claim 9, wherein the web has a height which is greater than a diameter of the line forming the coil.

* * * * *